(12) United States Patent
Rees et al.

(10) Patent No.: US 11,937,791 B2
(45) Date of Patent: Mar. 26, 2024

(54) DEVICE FOR SAMPLING GASTRO-INTESTINAL MATERIAL

(71) Applicant: BIOME OXFORD LIMITED, Woodstock (GB)

(72) Inventors: Samuel Rees, Rotherham (GB); Luke Ashton, Rotherham (GB); Chris Iveson, Rotherham (GB); Agnieszka Chomka, Marston (GB); Soren Thomsen, Marston (GB); Natasha Hui Jin Ng, Marston (GB); Patrick Albers, Marston (GB); Matthias Thurner, Marston (GB); Rasmus Aarup Poulsen, Marston (GB)

(73) Assignee: BIOME OXFORD LIMITED (GB)

( * ) Notice: Subject to any disclaimer, the term of this patent is extended or adjusted under 35 U.S.C. 154(b) by 545 days.

(21) Appl. No.: 16/336,931

(22) PCT Filed: Sep. 7, 2017

(86) PCT No.: PCT/GB2017/052613
§ 371 (c)(1),
(2) Date: Mar. 27, 2019

(87) PCT Pub. No.: WO2018/060673
PCT Pub. Date: Apr. 5, 2018

(65) Prior Publication Data
US 2019/0274663 A1 Sep. 12, 2019

(30) Foreign Application Priority Data
Sep. 28, 2016 (GB) ...................................... 1616464

(51) Int. Cl.
*A61B 10/00* (2006.01)
(52) U.S. Cl.
CPC .. *A61B 10/0045* (2013.01); *A61B 2010/0061* (2013.01)

(58) Field of Classification Search
CPC ........ A61B 10/0045; A61B 2010/0061; A61B 5/6861; A61B 2562/162; A61B 5/073;
(Continued)

(56) References Cited

U.S. PATENT DOCUMENTS

| 4,172,446 A | 10/1979 | Bucalo |
| 4,481,952 A | 11/1984 | Pawelec |

(Continued)

FOREIGN PATENT DOCUMENTS

| SU | 1202555 A1 * | 1/1986 | ............. A61B 10/00 |
| WO | WO 02/102243 | 12/2002 | |

(Continued)

OTHER PUBLICATIONS

Translation of Item N (SU 1202555 A1) (Year: 2024).*

*Primary Examiner* — Navin Natnithithadha
*Assistant Examiner* — Alice Ling Zou
(74) *Attorney, Agent, or Firm* — Bell & Manning, LLC (57) ABSTRACT

Devices for sampling gastro-intestinal material are disclosed. In one arrangement a device comprises a capsule body that has a sample input valve. A suction mechanism is provided that is capable of generating a partial vacuum within the capsule body and thereby drawing gastro-intestinal material into the capsule body through the sample input valve. An actuator actuates the suction mechanism. The actuator comprises a dissolvable element and is configured so that the dissolvable element dissolves in a predetermined region of the gastro-intestinal tract and the dissolving of the dissolvable element causes actuation of the suction mechanism. The suction mechanism comprises a biasing member restrained by the dissolvable element prior to actuation of the suction mechanism. The dissolving of the dissolvable element releases the biasing member. The biasing member expands a sample chamber within the capsule body on release of the biasing member, and generates the partial vacuum within the capsule body.

15 Claims, 4 Drawing Sheets

(58) Field of Classification Search
CPC ....... A61B 5/42; A61B 5/4238; A61B 5/4255; A61B 5/4283; A61B 10/0096
USPC ........................................................ 600/582
See application file for complete search history.

(56) References Cited

U.S. PATENT DOCUMENTS

| | | |
|---|---|---|
| 2003/0017195 A1 | 1/2003 | Mitragotri et al. |
| 2007/0173738 A1 | 7/2007 | Stoltz |
| 2008/0033569 A1 | 2/2008 | Ferren et al. |
| 2010/0286660 A1* | 11/2010 | Gross .................. A61B 5/4238 604/516 |
| 2015/0011874 A1 | 1/2015 | Amoako-Tuffour et al. |
| 2019/0298318 A1* | 10/2019 | Cinquin ............. A61B 10/0045 |

FOREIGN PATENT DOCUMENTS

| | | | |
|---|---|---|---|
| WO | WO 2005/046485 | 5/2005 | |
| WO | WO 2006/026504 | 3/2006 | |
| WO | WO 2014/140334 | 9/2014 | |
| WO | WO 2016/042302 | 3/2016 | |
| WO | WO-2018050647 A1 * | 3/2018 | ......... A61B 10/0038 |

* cited by examiner

DEVICE FOR SAMPLING GASTRO-INTESTINAL MATERIAL

CROSS REFERENCE TO RELATED APPLICATIONS

This application is a National Stage of International Application No. PCT/GB2017/052613, filed Sep. 7, 2017, which claims the benefit of GB Patent Application No. GB1616464.2, filed Sep. 28, 2016, the contents of which are herein incorporated by reference.

The invention relates to a device for sampling gastro-intestinal material.

Valuable information about the health of a subject can be obtained by analysing gastro-intestinal material. It is proven challenging however to extract gastro-intestinal material in a reliable and cost-effective manner, and without contaminating or otherwise disrupting the extracted material relative to its native state within the gastro-intestinal tract.

A promising approach has been to provide an ingestible device which can be opened to extract material at an appropriate position within the gastro-intestinal tract. An example of such a device is disclosed in US 2015/0011874 A1. The device uses a motor coupled to a rotatable element to open and close an access port to a chamber within the ingestible device which can store a sample of the material to be extracted. Electrical sensors are provided for sensing properties of the environment around the device. Opening of the access port by the motor can be triggered in response to an output from the electrical sensors. Ingestible devices of this type are relatively costly and complex.

It is an object of the invention to provide a device for sampling of gastro-intestinal material which has high reliability and low cost.

According to an aspect, there is provided a device for sampling gastro-intestinal material, comprising: a capsule body having a sample input valve; a suction mechanism configured to generate a partial vacuum within the capsule body and thereby draw gastro-intestinal material into the capsule body through the sample input valve; and an actuator configured to actuate the suction mechanism, wherein: the actuator comprises a dissolvable element and is configured so that the dissolvable element dissolves in a predetermined region of the gastro-intestinal tract and the dissolving of the dissolvable element causes actuation of the suction mechanism; the suction mechanism comprises a biasing member restrained by the dissolvable element prior to actuation of the suction mechanism; the dissolving of the dissolvable element releases the biasing member; and the biasing member is configured to expand a sample chamber within the capsule body, without any change to the outer shape and size of the capsule body, on release of the biasing member, and thereby generate the partial vacuum within the capsule body.

Thus, a device is provided which can actuate using purely mechanical means and with no need for mechanical or other links to the environment outside of body. The actuation mechanism is mechanically simple due to the reliance on dissolution of a dissolvable element, facilitating high reliability and low cost. No electrical input or machinery is required, either for actuation or for sensing properties of the environment. This also facilitates low cost and high reliability, as well as reducing the risk of injury or discomfort which may be caused by electrical elements and/or heat generated thereby. Arranging for the suction mechanism to comprise a biasing member restrained by the dissolvable element prior to actuation of the suction mechanism, such that dissolving of the dissolvable element releases the biasing member can be implemented particularly efficiently and reliably. The biasing member may be implemented using a spring for example. Springs are cheap and readily available in biocompatible materials.

In an embodiment, the sample input valve is configured to allow a pressure gradient driven passage of material from the outside of the capsule body to the inside of the capsule body through one or more sample collection openings, and to seal the one or more sample collection openings in the absence of a pressure gradient; and an exterior surface of the capsule body is provided with one or more indented channels leading to one or more of the sample collection openings to reduce blocking of the one or more sample collection openings by tissue or material within the gastro-intestinal tract. The indented channels thereby improve reliability.

In an embodiment, one or more of the sample collection openings is non-circular. This reduces or prevents blocking of sample collection openings by tissue or material (e.g. food particles) with the gastro-intestinal tract, thereby improving reliability.

In an embodiment, the device further comprises one or more protruding members protruding outwards relative to an average level of an outer surface of the capsule body adjacent to the sample input valve, for reducing suction-based adhesion of the device to tissue or material within the gastro-intestinal tract. This reduces or prevents blocking of sample collection openings, thereby improving reliability.

According to an alternative aspect, there is provided a device for sampling gastro-intestinal material, comprising: a capsule body having a sample input valve; a suction mechanism configured to generate a partial vacuum within the capsule body and thereby draw gastro-intestinal material into the capsule body through the sample input valve; and an actuator configured to actuate the suction mechanism, wherein: the actuator comprises a dissolvable element and is configured so that the dissolvable element dissolves in a predetermined region of the gastro-intestinal tract and the dissolving of the dissolvable element causes actuation of the suction mechanism; and the device is coated with a muco-adhesive material configured to promote adhesion between the device and a lining of the intestinal wall when the muco-adhesive material contacts the lining of the intestinal wall.

The adherence provided by the muco-adhesive material improves the stability of the device during the extraction of material into the device. In an embodiment, the muco-adhesive material is arranged on a portion of the outer surface of the device that is selected such that adhesion of the device to the lining of the intestinal wall is promoted in an orientation of the device which allows gastro-intestinal material to be drawn into the capsule body through the sample input valve. The orientation may be such that collection openings and actuator openings are not covered by any part of the lining of the intestinal wall when the device is adhered to the lining of the intestinal wall. Extraction of material by the device can therefore be carried out with high reliability.

Embodiments of the invention will now be described, by way of example only, with reference to the accompanying drawings in which corresponding reference symbols represent corresponding parts, and in which.

In an embodiment, an example of which is depicted in FIGS. 1-7, there is provided a device 2 for sampling gastro-intestinal material. Gastro-intestinal material encompasses any material found naturally within the gastro-intestinal tract.

Figure 1:
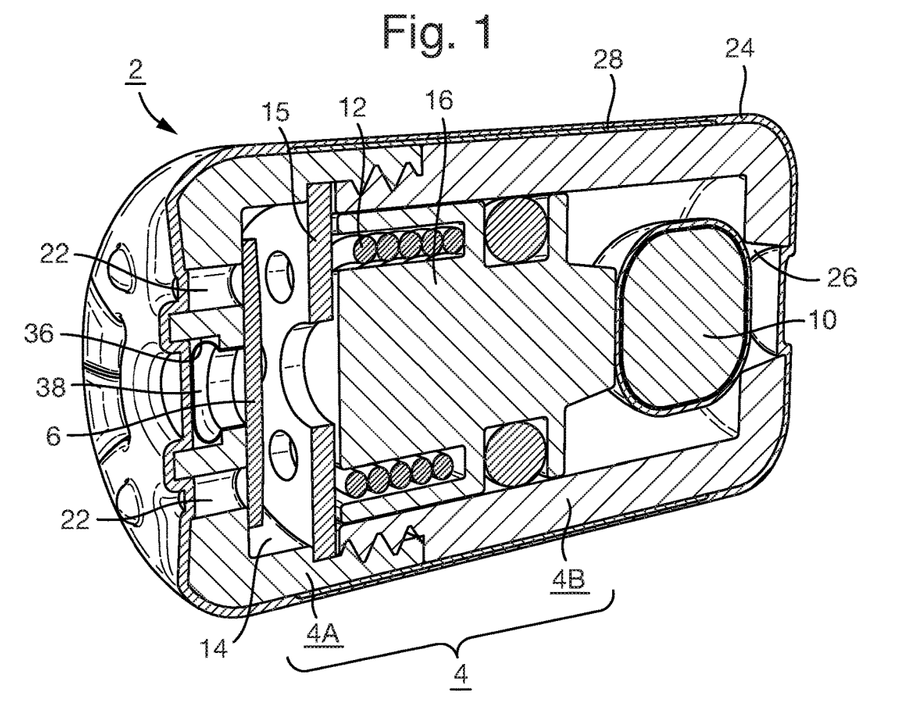
FIG. 1 is a perspective sectional view of a device for sampling gastro-intestinal material.
Figure 2:
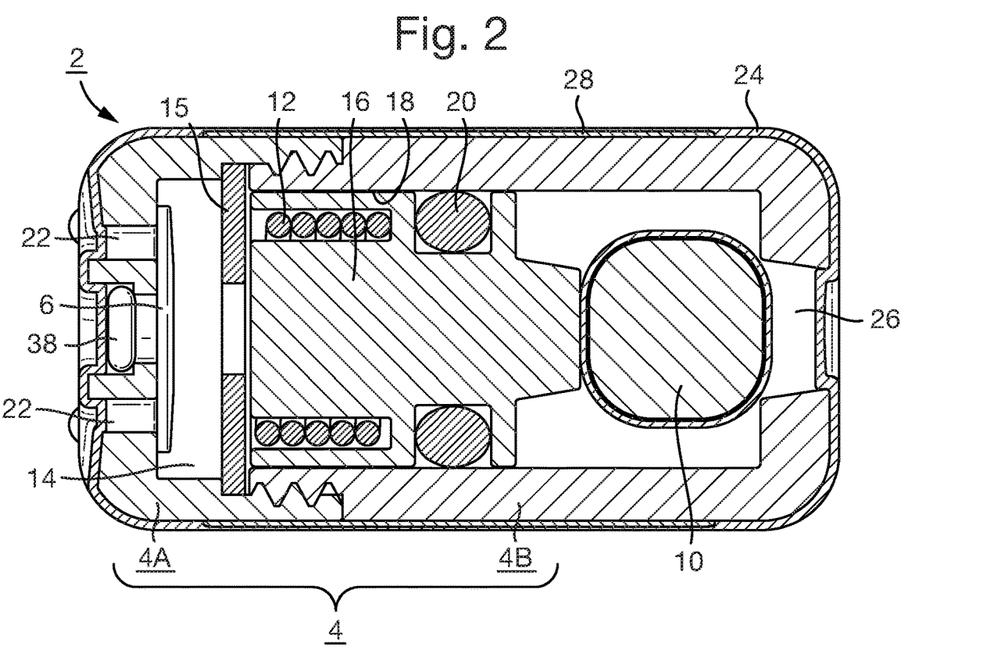
FIG. 2 is a side sectional view of the device of FIG. 1.

The device 2 comprises a capsule body 4 having a sample input valve 6. In an embodiment the sample input valve 6 comprises a one-way valve. In an embodiment the sample input value 6 comprises an umbrella valve, but other valve types could be used instead (e.g. duckbill valve). In the embodiment shown, the capsule body 4 comprises a front sub-unit 4A and a rear sub-unit 4B that can be screwed together for ease of assembly. Other arrangements for connecting together front and rear sub-units are possible, including for example a snap fastening mechanism, a pressure fitting, a ratchet mechanism or adhesive. The overall shape and size of the capsule body 4 is designed to be suitable for a human patient to swallow safely, and preferably without significant discomfort. Edges can be smoothed (rounded) to improve comfort and reduce risk of injury. In the embodiment shown the capsule body 4 has a substantially cylindrical form to allow space for a bore 18 within which a movable element 16 can move longitudinally (see below) without the overall dimensions of the device 2 becoming too large. In an embodiment the device 2 has an overall length of between 10 mm and 30 mm, optionally between 10 mm and 20 mm, optionally between 14 mm and 18 mm, optionally about 16 mm. In an embodiment the device 2 has a maximal diameter (perpendicular to the length direction) of between 6 mm and 12 mm, optionally between 6 mm and 10 mm, optionally between 7 mm and 9 mm, optionally about 8 mm.

The sample input valve 6 is secured within the front sub-unit 4A by means of a bung 38 of the sample input valve 6 engaging within an opening 36 in the front sub-unit 4A.

The device 2 further comprises a suction mechanism capable of generating a partial vacuum within the capsule body 4 and thereby drawing gastro-intestinal material into the capsule body 4 through the sample input valve 6. An actuator is provided for actuating the suction mechanism. The actuator comprises a dissolvable element 10. The actuator is configured so that the dissolvable element 10 dissolves in a predetermined region of the gastro-intestinal tract and the dissolving of the dissolvable element 10 causes actuation of the suction mechanism.

In the embodiment shown, the suction mechanism comprises a biasing member 12 restrained by the dissolvable element 10 prior to actuation of the suction mechanism. In the embodiment shown the biasing member 12 comprises a spring, but other mechanisms are possible. In the case where a spring is used the inventors have found that a compression spring arrangement is more practical than a tension spring arrangement, as it makes better use of the small amount of space available. Springs are relatively cheap and readily available in biocompatible materials. Springs can also be provided in a suitably small size to fit within the device 2 while still providing the necessary forces to achieve actuation. The biasing member 12 presses against a support member 15 (having holes to allow material to flow through the support member 15) that is fixedly attached to the capsule body 4. The provision of the support member 15 prevents the biasing member 12 from pressing against, or otherwise interfering with, the sample input valve 6. The dissolving of the dissolvable element 10 releases the biasing member 12. The biasing member 12 expands a sample chamber 14 within the capsule body 4 on release of the biasing member 12 and thereby generates the partial vacuum within the capsule body 4. The expansion of the capsule body 4 is achieved without any change in the overall (i.e. outer) size and shape of the capsule body 4 (i.e. without any change in the size and shape of the exterior surface of the capsule body 4) and, therefore, without any change in the overall size and shape of the device 2. Risk of injury or discomfort that might otherwise be caused by expansion of the device 2 during actuation are therefore reduced. Furthermore, reproducibility and reliability of the actuation process are improved because all moving parts are mechanically isolated from the surrounding environment. Moving parts cannot press against elements in the surrounding environment or be pressed against by elements in the surrounding environment. In the embodiment shown, the suction mechanism comprises a movable element 16 engaged within a bore 18 via a sliding seal 20. The biasing member 12 expands the sample chamber 14 by driving movement of the movable element 16 within the bore 18. In the example shown, the movable element 16 comprises a cylindrical piston and the bore 18 comprises a cylindrical bore, with the cylindrical piston being slidably engaged within the cylindrical bore (in the manner of a standard piston and cylinder).

In the embodiment shown the sliding seal 20 is implemented by means of an o-ring engaging outwardly against the bore 18. Various materials can be used for the o-ring, including for example nitrile (NBR), silicone, fluorocarbon (FKM), ethylene propylene (EPDM), isoprene rubber (IR), and thermoplastic (TP). It is desirable to provide a relatively small sliding seal force (i.e. force resisting movement in the sliding direction). Providing a relatively small sliding seal force means that the biasing member 12 can be configured to provide a smaller force. The risk of injury in the event of failure of the device is thereby reduced.

The sample input valve 6 is configured to allow a pressure gradient driven passage of material from the outside of the capsule body 4 to the inside of the capsule body 4 through sample collection openings 22, and to seal the sample collection openings 22 in the absence of a pressure gradient (i.e. to be driven by the absence of the pressure gradient to provide the seal, for example because the pressure gradient no longer acts against an intrinsic bias of the sample input valve 6 to the sealed state). Thus, when the partial vacuum is generated by the biasing member 12, the pressure gradient thereby generated opens the sample input valve 6 (see FIG. 6) and allows material to be driven by the pressure gradient into the sample chamber 14 until the pressure gradient falls to a level which is no longer high enough to hold the sample input valve 6 open (see FIG. 7). At this point the sample input valve 6 closes and the extracted material is sealed within the sample chamber 14 ready for removal and analysis at a later time.

In the embodiment shown, the capsule body 4 comprises an actuator opening 26 (more than one actuator opening may be provided in other embodiments) via which the gastro-intestinal material can contact the dissolvable element 10 and dissolve the dissolvable element 10 when the actuator opening 26 is unsealed. The actuator opening 26 is separated from the sample collection openings 22, thereby reducing or avoiding contamination of the material extracted into the sample chamber 14 by material originating from the dissolvable element 10. In the embodiment shown the risk of contamination is further reduced or avoided by providing the actuator opening 26 on an opposite side of the capsule body 4 to the sample collection openings.

In an embodiment the device 2 is configured to be taken orally. For example, the actuator is configured so that the dissolvable element 10 remains intact during transit from the mouth to the predetermined region at which it is desired to extract material, and dissolves in the predetermined region. This may be achieved by coating the device 2 and/or dissolvable element 10 in such a way that the device and/or dissolvable element 10 only become uncovered when the device 2 is in the predetermined region. Alternatively or additionally, the dissolvable element 10 may be configured such that it is resistant to material in the gastro-intestinal tract in all regions prior to the predetermined region at which it is desired to extract material but dissolves in material present in the predetermined region.

The device 2 is thus actuated based on selectively dissolving the dissolvable member 10 in the predetermined region (and not before). Various differences in the composition of material found in different regions of the gastro-intestinal tract may be used as the basis for achieving the selective dissolving. For example, there is a large pH gradient between the stomach and the small intestine, which can be used to ensure actuation of the device 2 in the small intestine (or even in a specific region of the small intestine). Various different coatings are available commercially that dissolve at different pH levels and which would allow such targeting. The pH gradient is much smaller between the small intestine and the large intestine, which may favour use of non-pH based methods of achieving the selective dissolving. In one embodiment, a coating is used which is broken down by one or more enzymes which are found in the predetermined region of interest (e.g. the large intestine) and not in any earlier portion of the gastro-intestinal tract (e.g. section of the small intestine or stomach).

In the embodiment shown, the device 2 is entirely encapsulated by a sealing material 24 that is configured such that when the device is taken orally, the sealing material 24 will dissolve only when the device 2 reaches the predetermined region of the gastro-intestinal tract. It is not essential for the sealing material 24 to entirely encapsulate the device 2. In other embodiments the sealing material 24 may only partially encapsulate the device 2. For example, the sealing material 24 may cover (and thereby seal until it dissolves) the actuator opening 26 and not cover selected other regions of the outer surface of the device 2. Alternatively or additionally, the sealing material 24 may cover (and thereby seal until it dissolves) the sample collection openings 22. In an embodiment the sealing material 24 comprises an enteric coating. The sealing material 24 may be applied by spray coating, for example.

The dissolvable element 10 is formed from a material that is safe for consumption and does not significantly modify the gut microbiome (i.e. materials containing sugar or other materials which may be consumed by bacteria should be avoided). The dissolvable element 10 also needs to be dissolvable, at least in the material found in the predetermined region (optionally in other liquids where the dissolvable element 10 is coated). Various materials are suitable, including one or more of the following in any combination: hypromellose, polyvinylpyrrolidone, sodium carboxymethyl cellulose, and sodium starch glycolate. The dissolvable element 10 may be solid or hollow.

In an embodiment, the dissolvable element 10 comprises a first material coated with a second material. The first material may be fully encapsulated by the second material. The second material may be configured such that when the device 2 is taken orally, the second material will dissolve only when the device 2 reaches the predetermined region of the gastro-intestinal tract. The second material may comprise an enteric coating for example. The first material provides the necessary bulk for the dissolvable element 10 to mechanically restrain the biasing member 12, while the second material provides the selective dissolving functionality necessary to ensure that the device 2 actuates in the desired predetermined region of the gastro-intestinal tract.

Other coatings may be provided to the device 2 to improve functionality. For example, in an embodiment the device is coated with a muco-adhesive material 28 configured to promote adhesion between the device 2 and a lining of the intestinal wall when the muco-adhesive material 28 contacts the lining of the intestinal wall. In the example shown in FIGS. 1 and 2 the muco-adhesive material 28 is covered initially by the sealing material 24 so that the muco-adhesive material 28 only becomes exposed (and thereby prone to adhering to the lining of the intestinal wall) in the predetermined region of the gastro-intestinal tract. The adherence provided by the muco-adhesive material 28 improves the stability of the device 2 during the extraction of material into the sample chamber 14. The adhesion is not strong enough to prevent the device 2 from being passed through the gastro-intestinal tract nor to risk any damage to the gastro-intestinal tract. Various materials, including for example polymers, lectins, and liposome-based formulations are known which provide the required functionality. Non-limiting examples developed for oral delivery include: chitosan, poly(acrylic acid), alginate, poly(methacrylic acid) and sodium carboxymethyl cellulose.

In the embodiment shown the muco-adhesive material is arranged on a portion of the outer surface of the device 2 that is selected such that adhesion of the device 2 to the lining of the intestinal wall is promoted in an orientation of the device 2 which allows gastro-intestinal material to be drawn into the capsule body through the sample input valve 6. The orientation may be such that both collection openings 22 and actuator openings 26 are not covered by any part of the lining of the intestinal wall when the device 2 is adhered to the lining of the intestinal wall. In the embodiment shown this is achieved by providing the muco-adhesive material on an outer lateral surface that is substantially perpendicular to the surface in which the sample collection openings 22 are provided and substantially perpendicular to the surface in which the actuator opening 26 is provided, but it will be appreciated that other arrangements are possible, depending on the particular geometry of the device 2 and the positioning of the collection openings 22 and actuator openings 26.

Various features may be provided to promote efficient extraction of material through the collection openings 22. An example configuration for a front sub-unit 4A of the capsule body 4, comprising examples of such features, is shown in FIG. 3.

Figure 3:
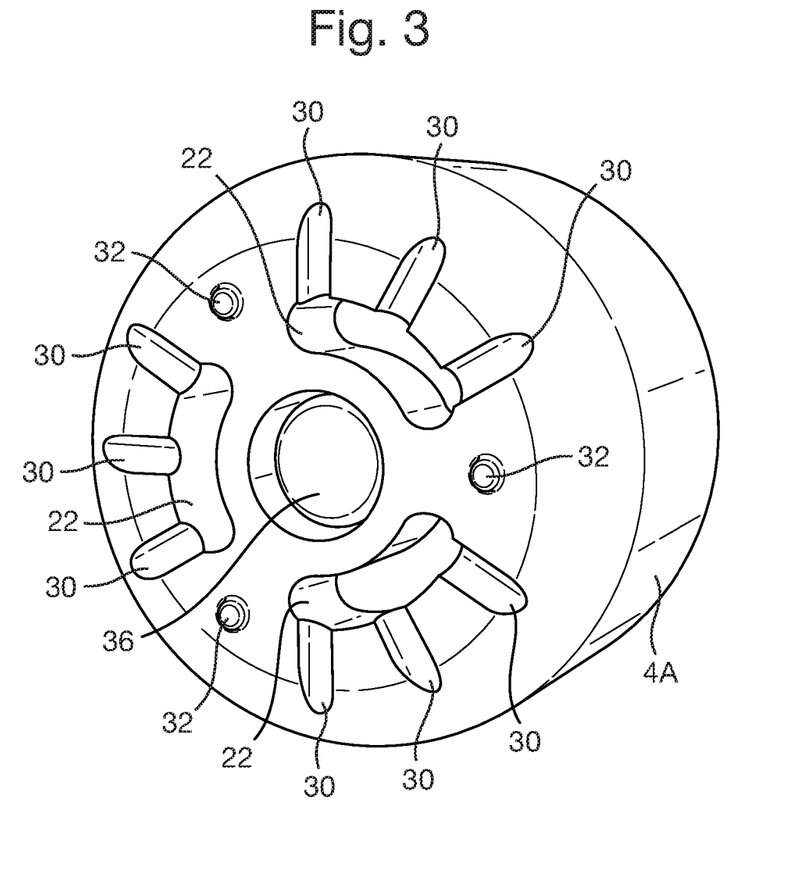
FIG. 3 is a perspective view of a front sub-unit of the capsule body of the device of FIGS. 1 and 2, showing example indented channels and protruding members.

In an embodiment, as depicted in FIG. 3, an exterior surface of the front sub-unit 4A is provided with indented channels 30. Each of the indented channels 30 leads to one of three sample collection openings 22 in this particular example. Other arrangements are possible (e.g. different numbers of sample collection openings and/or indented channels 30). The indented channels 30 are configured to reduce or prevent blocking of the sample collection openings 22 by tissue or material (e.g. food particles) within the gastro-intestinal tract.

In order to further reduce or prevent blocking of the sample collection openings 22, one or more of the sample collection openings 22 may be non-circular, for example elongate. In the embodiment shown, three such non-circular (and elongate) collection openings 22 are provided.

In an embodiment, as depicted in FIG. 3, one or more protruding members 32 are provided. The protruding members 32 protrude outwards relative to an average level of an outer surface of the capsule body 4 adjacent to the sample input valve 6 (and collection openings 22). The protruding members 32 are configured to reducing suction-based adhesion of the device 2 to tissue or material within the gastro-intestinal tract. The protruding members 32 prevent any large substantially planar surface being available that could otherwise become attached via suction-based adhesion to tissue or material within the gastro-intestinal tract, thereby potentially blocking (partially or completely) one or more of the collection openings 22. The protruding members 32 effectively allow the device 2 to stand away from the intestinal wall and allow fluid to flow in between (preventing the build up of any vacuum).

FIGS. 4-7 illustrate operation of the embodiment described above with reference to FIGS. 1-3.

Figure 4:
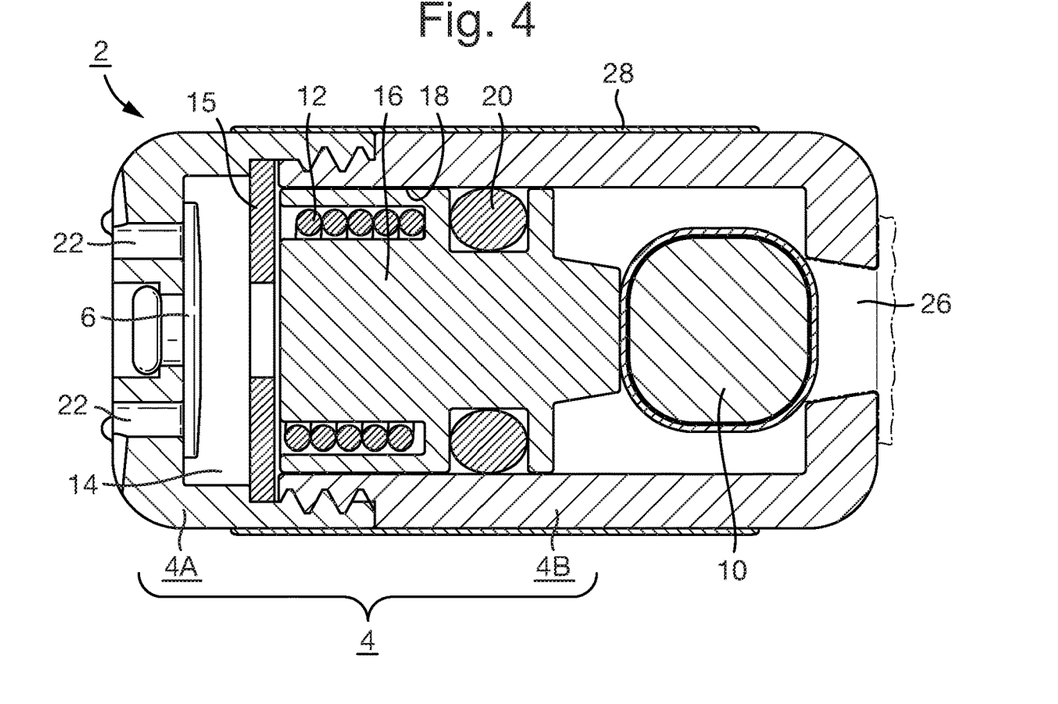
FIGS. 4-7 are side sectional views of the device of FIGS. 1 and 2 at different stages of actuation.

FIG. 4 depicts the device 2 after it has reached the predetermined region in the gastro-intestinal tract and the sealing material 24 (shown in FIGS. 1 and 2) has dissolved away. For example, the sealing material 24 may comprise an enteric coating that protects the device 2 from the acidic environment in the stomach until it passes through into the small intestine. Once in the small intestine the pH levels rise due to the introduction of bile and sodium carbonate. This causes the sealing material 24 to dissolve. The dissolving of the sealing material 24 exposes the collection openings 22, the muco-adhesive material 28 and the dissolvable element 10 to material at the predetermined region in the gastro-intestinal tract.

Figure 5:
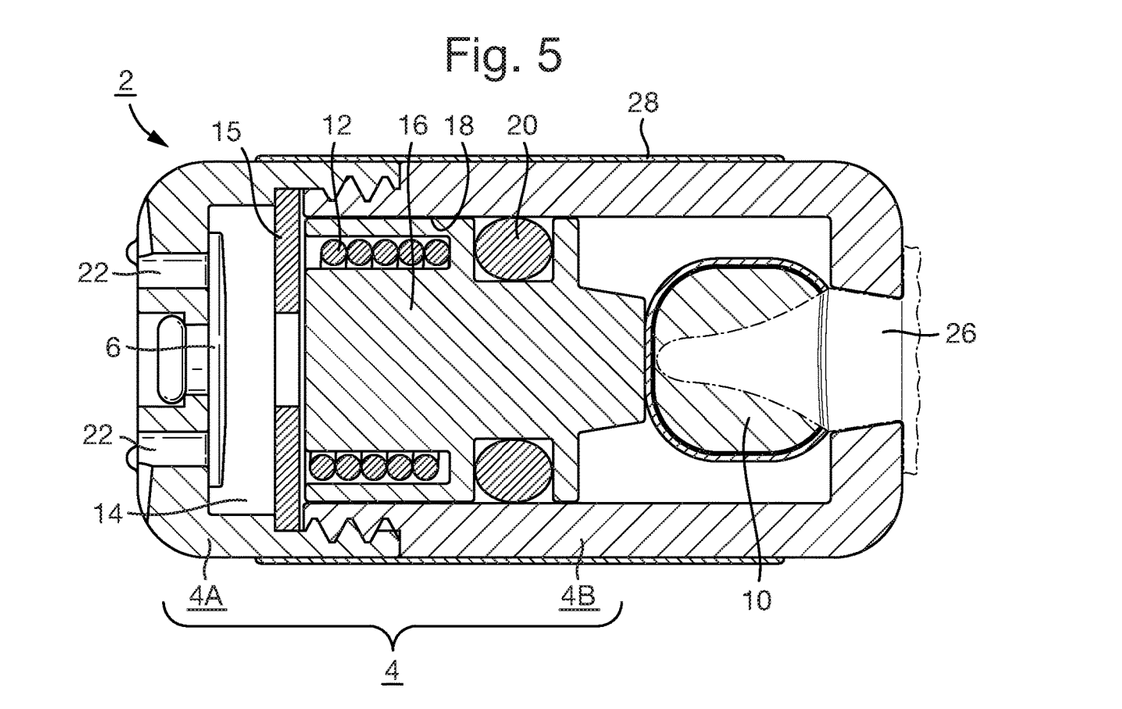

FIG. 5 depicts the device 2 at a subsequent time when the dissolvable element 10 has started to dissolve. The dissolvable element 10 is shaped so that the dissolution occurs at the desired rate and achieves the desired aim of actuating the device 2.

Figure 6:
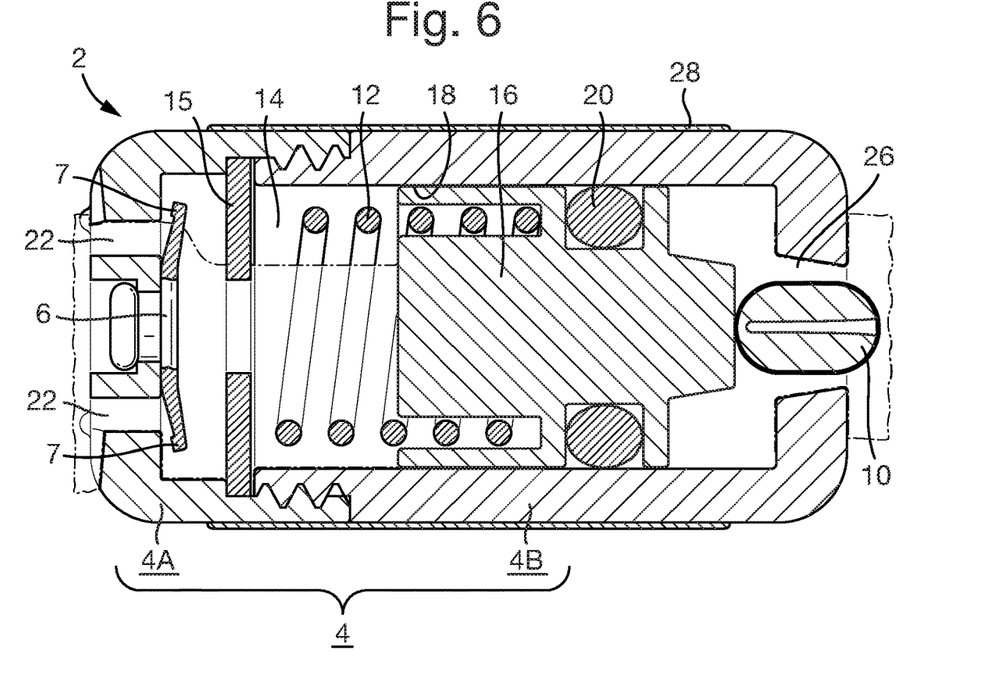

FIG. 6 depicts the device 2 at a subsequent time when the shape of the dissolvable element 10 has changed due to the dissolution (e.g. partially collapsed) in such a way that the biasing member 12 is released. The released biasing member 12 pushes the movable element 16 to the right in the orientation of the figure. The sample chamber 14 is expanded. The expansion generates a partial vacuum in the sample chamber 14. The partial vacuum provides a pressure gradient between the outside of the device 2 and the sample chamber 14. The pressure gradient forces open the sample input valve 6 (depicted in FIG. 6 by the pulling back of the peripheral edges 7 of the sample input valve 6). Opening of the sample input valve 6 allows material to be driven by the pressure gradient into the sample chamber 14.

Figure 7:
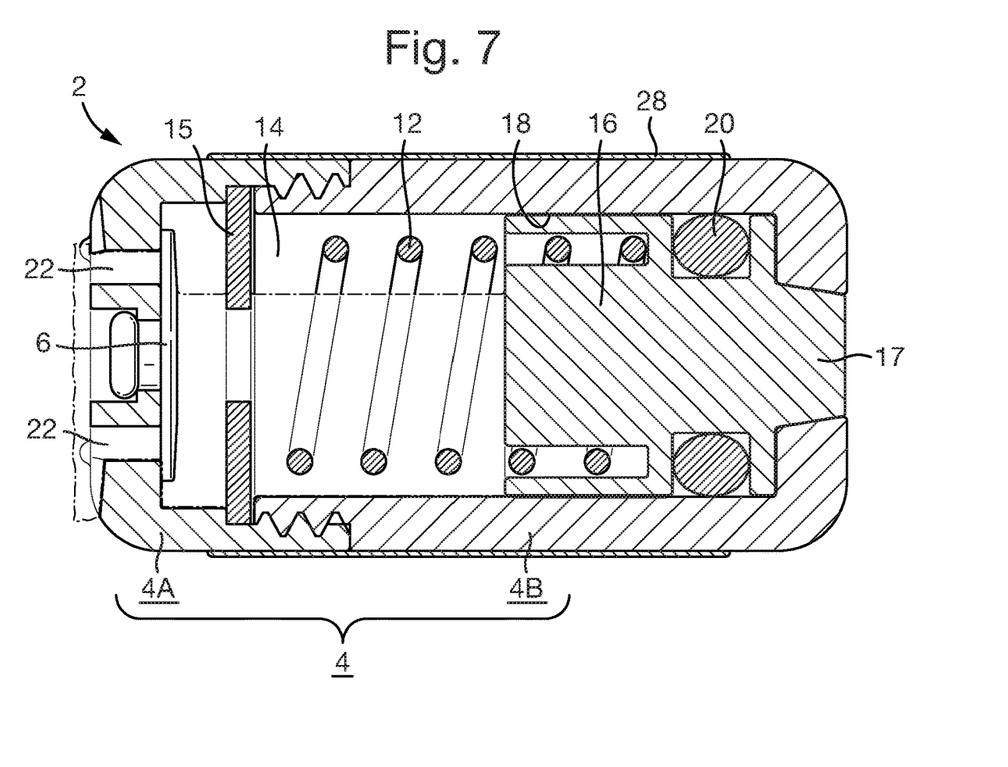

FIG. 7 depicts the device 2 after the actuation process is complete. The movable element 16 has been pushed all the way to the extreme end of its travel, sealing the actuator opening 26 via a portion 17 having a form complementary to the form of the actuator opening 26. The pressure difference between the sample chamber 14 and the outside of the device 2 is now low enough that the sample input valve 6 is closed. The sample chamber 14 is filled with material extracted from the predetermined region of the gastro-intestinal tract, as desired, and sealed, ready for removal and analysis at a later time.

In an embodiment the sample chamber 14 may be pre-filled (optionally partially) with a substance (e.g. a preservative), which acts in a desirable way on material that has been extracted into the sample chamber 14 during the time between extraction from the gastro-intestinal tract and removal for analysis at a later time (e.g. preventing or reducing degradation of the extracted material).

Aspects of the disclosure may additionally be described by the following numbered clauses:

1. A device for sampling gastro-intestinal material, comprising:
    a capsule body having a sample input valve;
    a suction mechanism configured to generate a partial vacuum within the capsule body and thereby draw gastro-intestinal material into the capsule body through the sample input valve; and
    an actuator configured to actuate the suction mechanism, wherein:
    the actuator comprises a dissolvable element and is configured so that the dissolvable element dissolves in a predetermined region of the gastro-intestinal tract and the dissolving of the dissolvable element causes actuation of the suction mechanism.

2. The device of clause 1, wherein the device is configured to be taken orally.

3. The device of clause 2, wherein the actuator is configured so that the dissolvable element remains intact during transit from the mouth to the predetermined region and dissolves in the predetermined region.

4. The device of any of clauses 1-3, wherein:
    the suction mechanism comprises a biasing member restrained by the dissolvable element prior to actuation of the suction mechanism; and
    the dissolving of the dissolvable element releases the biasing member.

5. The device of clause 4, wherein the biasing member is configured to expand a sample chamber within the capsule body on release of the biasing member and thereby generate the partial vacuum within the capsule body.

6. The device of clause 5, wherein the suction mechanism comprises a movable element engaged within a bore via a sliding seal, and the biasing member is configured to expand the sample chamber by driving movement of the movable element within the bore.

7. The device of any of clauses 4-6, wherein the biasing member comprises a spring.

8. The device of any of clauses 1-7, wherein the device is coated with a muco-adhesive material configured to promote adhesion between the device and a lining of the intestinal wall when the muco-adhesive material contacts the lining of the intestinal wall.

9. The device of clause 8, wherein the muco-adhesive material is coated so as only to become exposed when the device reaches the predetermined region of the gastro-intestinal tract.

10. The device of any of clauses 1-9, wherein the sample input valve is configured to allow a pressure gradient driven passage of material from the outside of the capsule body to the inside of the capsule body through one or more sample collection openings, and to seal the one or more sample collection openings in the absence of a pressure gradient.

11. The device of clause 10, wherein the capsule body comprises one or more actuator openings via which the gastro-intestinal material can contact the dissolvable element and dissolve the dissolvable element when the one or more actuator openings are unsealed, wherein the one or more actuator openings are separated from the one or more sample collection openings.

12. The device of clause 11, wherein the one or more actuator openings are on an opposite side of the capsule body to the one or more sample collection openings.

13. The device of clause 11 or 12, wherein the one or more actuator openings are sealed by a sealing material, the sealing material being configured such that when the device is taken orally, the sealing material will dissolve only when the device reaches the predetermined region of the gastro-intestinal tract.

14. The device of clause 13, wherein the device is coated with a muco-adhesive material configured to promote adhesion between the device and a lining of the intestinal wall when the muco-adhesive material contacts the lining of the intestinal wall.

15. The device of clause 14, wherein the sealing material is provided over the muco-adhesive material, such that the muco-adhesive material is exposed only when the device reaches the predetermined region of the gastro-intestinal tract.

16. The device of any of clauses 13-15, wherein the sealing material comprises an enteric coating.

17. The device of any of clauses 8, 9 and 14-16, wherein the muco-adhesive material is arranged on a portion of the outer surface of the device that is selected such that adhesion of the device to the lining of the intestinal wall is promoted in an orientation of the device which allows gastro-intestinal material to be drawn into the capsule body through the sample input valve.

18. The device of any of clauses 1-17, wherein:
the sample input valve is configured to allow a pressure gradient driven passage of material from the outside of the capsule body to the inside of the capsule body through one or more sample collection openings, and to seal the one or more sample collection openings in the absence of a pressure gradient; and
an exterior surface of the capsule body is provided with one or more indented channels leading to one or more of the sample collection openings to reduce blocking of the one or more sample collection openings by tissue or material within the gastro-intestinal tract.

19. The device of any of clauses 1-18, wherein:
the sample input valve is configured to allow a pressure gradient driven passage of material from the outside of the capsule body to the inside of the capsule body through one or more sample collection openings, and to seal the one or more sample collection openings in the absence of a pressure gradient; and
one or more of the sample collection openings is non-circular.

20. The device of any of clauses 1-19, further comprising one or more protruding members protruding outwards relative to an average level of an outer surface of the capsule body adjacent to the sample input valve, for reducing suction-based adhesion of the device to tissue or material within the gastro-intestinal tract.

21. The device of any of clauses 1-20, wherein the dissolvable element comprises one or more of the following: hypromellose, polyvinylpyrrolidone, sodium carboxymethyl cellulose, and sodium starch glycolate.

22. The device of any of clauses 1-21, wherein the dissolvable element comprises a first material coated with a second material.

23. The device of clause 22, wherein the first material is fully encapsulated by the second material.

24. The device of clause 22 or 23, wherein the second material is configured such that when the device is taken orally, the second material will dissolve only when the device reaches the predetermined region of the gastro-intestinal tract.

25. The device of any of clauses 22-24, wherein the second material comprises an enteric coating.

The invention claimed is:

1. A device for sampling gastro-intestinal material, comprising:
a capsule body comprising a sample input valve, the sample input valve comprising a one-way valve;
a suction mechanism configured to generate a partial vacuum; and
an actuator configured to actuate the suction mechanism, wherein:
the actuator comprises a dissolvable element and is configured so that the dissolvable element dissolves in a predetermined region of the gastro-intestinal tract and the dissolving of the dissolvable element causes actuation of the suction mechanism;
the suction mechanism comprises a biasing member restrained by the dissolvable element prior to actuation of the suction mechanism;
the dissolving of the dissolvable element releases the biasing member;
the biasing member is configured to expand a sample chamber within the capsule body, on release of the biasing member, such that the outer shape and size of the device is the same after expansion of the sample chamber as the outer shape and size of the device prior to expansion of the sample chamber and thereby generate the partial vacuum within the sample chamber and draw gastro-intestinal material into the sample chamber through the sample input valve; and
the sample input valve is configured to allow a pressure gradient driven passage of the gastro-intestinal material from the outside of the capsule body into the sample chamber through one or more sample collection openings, and, in the absence of a pressure gradient, to be driven to seal the one or more sample collection openings by the absence of the pressure gradient; and
the capsule body comprises an actuator opening via which the gastro-intestinal material can contact the dissolvable element and dissolve the dissolvable element, wherein the dissolvable element is positioned to fully seal the actuator opening prior to expansion of the sample chamber, wherein the biasing member forces a movable element to push the dissolvable element through the actuator opening during expansion of the sample chamber, and wherein upon pushing the dissolvable element through the actuator opening the movable element is positioned to fully seal the actuator opening such that only the dissolvable element exits through the actuator opening during expansion of the sample chamber, and wherein the one or more actuator openings are separated from the one or more sample collection openings.

2. The device of claim 1, wherein:
the device is configured to be taken orally; and
the actuator is configured so that the dissolvable element remains intact during transit from the mouth to the predetermined region and dissolves in the predetermined region.

3. The device of claim 1, wherein the suction mechanism comprises the movable element engaged within a bore via a sliding seal, and the biasing member is configured to expand the sample chamber by driving movement of the movable element within the bore.

4. The device of claim 3, wherein the movable element comprises a cylindrical piston and the bore comprises a cylindrical bore, the cylindrical piston being slidably engaged within the cylindrical bore.

5. The device of claim 1, wherein the device is coated with a muco-adhesive material configured to promote adhesion between the device and a lining of the intestinal wall when the muco-adhesive material contacts the lining of the intestinal wall.

6. The device of claim 5, wherein the muco-adhesive material is coated with a further material so as only to become exposed when the device reaches the predetermined region of the gastro-intestinal tract.

7. The device of claim 5, wherein the muco-adhesive material is arranged on a portion of the outer surface of the device that is selected such that adhesion of the device to the lining of the intestinal wall is promoted in an orientation of the device which allows gastro-intestinal material to be drawn into the capsule body through the sample input valve.

8. The device of claim 1, wherein the actuator opening is on an opposite side of the capsule body to the one or more sample collection openings.

9. The device of claim 1, wherein the actuator opening is sealed by a sealing material, the sealing material being configured such that when the device is taken orally, the sealing material will dissolve only when the device reaches the predetermined region of the gastro-intestinal tract.

10. The device of claim 9, wherein:
the device is coated with a muco-adhesive material configured to promote adhesion between the device and a lining of the intestinal wall when the muco-adhesive material contacts the lining of the intestinal wall.

11. The device of claim 1, wherein
an exterior surface of the capsule body is provided with one or more indented channels leading to one or more of the sample collection openings to reduce blocking of the one or more sample collection openings by tissue or material within the gastro-intestinal tract.

12. The device of claim 1, wherein
one or more of the sample collection openings is non-circular.

13. The device of claim 1, further comprising one or more protruding members protruding outwards relative to an average level of an outer surface of the capsule body adjacent to the sample input valve, for reducing suction-based adhesion of the device to tissue or material within the gastro-intestinal tract.

14. The device of claim 1, wherein the dissolvable element comprises a first material coated with a second material.

15. The device of claim 14, wherein the second material is configured such that when the device is taken orally, the second material will dissolve only when the device reaches the predetermined region of the gastro-intestinal tract.

* * * * *